United States Patent [19]

Walsh

[11] Patent Number: 4,633,864
[45] Date of Patent: Jan. 6, 1987

[54] SPEAKING ENDOTRACHEAL TUBE

[75] Inventor: John J. Walsh, LaCrescent, Minn.

[73] Assignee: Dacomed Corporation, Minneapolis, Minn.

[21] Appl. No.: 663,578

[22] Filed: Oct. 22, 1984

[51] Int. Cl.⁴ ............................................. A61M 16/00
[52] U.S. Cl. .................................... 128/207.15; 623/9
[58] Field of Search ...................... 128/207.14, 207.15, 128/207.16, 200.26, 207.18; 3/1.3; 623/9

[56] References Cited

U.S. PATENT DOCUMENTS

| | | |
|---|---|---|
| 2,273,077 | 2/1942 | Wright ..................................... 3/1.3 |
| 2,643,848 | 6/1953 | Hoffman . |
| 2,786,469 | 3/1957 | Cohen . |
| 3,169,529 | 2/1965 | Koenig . |
| 3,322,126 | 5/1967 | Rusch et al. . |
| 3,334,631 | 8/1967 | Stebleton . |
| 3,363,629 | 1/1968 | Kuhn . |
| 3,402,717 | 9/1968 | Doherty . |
| 3,402,718 | 9/1968 | Doherty . |
| 3,438,375 | 4/1969 | Ericson . |
| 3,443,964 | 5/1969 | Oehmig . |
| 3,460,541 | 8/1969 | Doherty . |
| 3,481,339 | 12/1969 | Puig . |
| 3,504,676 | 4/1970 | Lomholt . |
| 3,529,596 | 9/1970 | Garner . |
| 3,565,079 | 2/1971 | Jackson . |
| 3,587,589 | 6/1971 | Ebner . |
| 3,605,750 | 9/1971 | Sheridan et al. . |
| 3,625,793 | 12/1971 | Sheridan et al. . |
| 3,642,005 | 2/1972 | McGinnis . |
| 3,659,611 | 5/1972 | Miller . |
| 3,693,624 | 9/1972 | Shiley et al. . |
| 3,731,691 | 5/1973 | Chen . |
| 3,769,983 | 11/1973 | Merav . |
| 3,771,527 | 11/1973 | Ruisi . |
| 3,788,326 | 1/1974 | Jacobs . |
| 3,794,036 | 2/1974 | Carroll . |
| 3,794,043 | 2/1974 | McGinnis . |
| 3,810,474 | 5/1974 | Cross . |
| 3,848,605 | 11/1974 | Harautuneian et al. . |
| 3,889,688 | 6/1975 | Eamkaow . |
| 3,901,246 | 8/1975 | Wallace . |
| 3,948,274 | 4/1976 | Zeldman et al. . |
| 3,973,569 | 8/1976 | Sheridan et al. . |
| 3,987,798 | 10/1976 | McGinnis . |
| 4,009,720 | 3/1977 | Crandall . |
| 4,033,353 | 7/1977 | La Rosa . |
| 4,037,605 | 7/1977 | Firth . |
| 4,156,428 | 5/1979 | Henkin . |
| 4,159,722 | 7/1979 | Walker . |
| 4,235,229 | 11/1980 | Ranford et al. . |
| 4,240,417 | 12/1980 | Holever . |
| 4,246,897 | 1/1981 | Muto . |
| 4,270,778 | 6/1981 | Brownell . |
| 4,278,081 | 7/1981 | Jones . |
| 4,280,492 | 7/1981 | Latham . |
| 4,315,505 | 2/1982 | Crandall et al. . |
| 4,324,235 | 4/1982 | Beran . |
| 4,327,720 | 5/1982 | Bronson et al. . |
| 4,327,721 | 5/1982 | Goldin et al. . |
| 4,331,142 | 5/1982 | Degen . |
| 4,340,046 | 7/1982 | Cox . |
| 4,344,436 | 8/1982 | Kubota ........................... 128/207.15 |
| 4,378,796 | 4/1983 | Milhand ......................... 128/207.15 |
| 4,449,523 | 5/1984 | Szachowicz et al. .......... 128/207.15 |
| 4,489,440 | 12/1984 | Chaoui .................................... 3/1.3 |

FOREIGN PATENT DOCUMENTS

| | | |
|---|---|---|
| 82651 | 6/1983 | European Pat. Off. ................. 3/1.3 |
| 693510 | 7/1953 | United Kingdom . |
| 198527 | 12/1967 | U.S.S.R. . |

OTHER PUBLICATIONS

R. Carrat, "Canule Tracheale Permettant la Phonation Pendant la Ventilation Artificielle par Tracheotomie", Anesth. Analg., (PAR), vol. 16, pp. 597-598, Jun.-Aug. 1959.

(List continued on next page.)

Primary Examiner—Henry J. Recla
Attorney, Agent, or Firm—Merchant, Gould, Edell, Welter & Schmidt

[57] ABSTRACT

An endotracheal tube (10) including, in addition to a primary ventilating channel (11), a secondary speaking channel (12). The speaking channel (12) contains an array of exit ports (16) for the introduction of a tone into the posterior oral pharynx (23) of the intubated patient. This tone is then conducted into the oral cavity (18) wherein it is articulated into speech by the patient. This substitute vocal sound is produced by a tone generating device (19) connected to and in air communication with the speaking channel (12) of the present invention.

19 Claims, 3 Drawing Figures

OTHER PUBLICATIONS

Safar et al., "Cuffed Tracheotomy Tube vs. Tank Respirator for Prolonged Artificial Ventilation", *Archives of Physical Medicine and Rehabilitation*, vol. 93, pp. 487–493, Oct. 1962.

Jackson, "New Type of Tube for Tracheotomy with Inflatable Cuff and Inner Cannula", *Journal of Neurosurgery*, vol. 20, p. 809, Jan.–Dec. 1963.

P. Carrat, "La Phonation au Cours de la Ventilation Pulmonaire Artificielle par Tracheotomie", *Revue Laryne*, Bordeauf, vol. 84, pp. 517–520, Jul.–Aug. 1963.

Hessler et al., "Tracheostomy Cannula for Speaking During Artificial Respiration", *Anesthesiology*, vol. 25, No. 5, pp. 719–721, Sep.–Oct. 1964.

"A Means of Speaking for Patients with Cuffed Tracheostomy Tubes", *British Medical Journal*, vol. 3, p. 547, Aug. 1967.

Obier et al., "Enhancing Therapeutic Communication with Acutely Ill Patients", *Heart and Lung*, vol. 2, No. 1, pp. 49–53, Jan.–Feb. 1973.

Lawless, "Helping Patients with Endotracheal and Tracheostomy Tubes Communicate", *American Journal of Nursing*, vol. 75, No. 12, pp. 2151–2153, Dec. 1975.

Hansen et al., "Vocalisation Via a Cuffed Tracheostomy Tube", *Anesthesia*, vol. 30, pp. 78–79, 1975.

Safar et al., "Speaking Cuffed Tracheostomy Tube", *Critical Care Medicine*, vol. 3, No. 1, pp. 23–26, Jan.–Feb. 1975.

Japanese Journal of Anesthesiology, vol. 25, No. 12, pp. 1312–1315, Nov. 1976.

Portex, Inc., "Trach Talk Tube", catalog, p. 199.

"New Inventions: A Tracheotomy Tube for Use in Acute Poliomyelitis", *The Lancet*, Jan. 7, 1956, p. 26.

"The Patient Requiring Mechanical Ventilatory Support: Use of the Cuffed Tracheostomy Talk Tube to Establish Phonation", Kluin, Maynard, Bogdasarian, presented at Annual Mtg. of Amer. Academy of Otolaryngology—Head & Neck Surgery, Anaheim, CA, Oct. 23–27, 1983.

SPEAKING ENDOTRACHEAL TUBE

BACKGROUND

1. Field of the Invention.

The present invention relates generally to endotracheal tubes, and artificial voicing systems.

2. Background of the invention.

Since the advent of ventilatory assistance with an endotracheal tube, patients have had to accept the sacrifice of speech that results from the tube being placed in the patient's trachea through the vocal cords. This loss of speech may result in great fear, frustration and withdrawal of the intubated patient. Also, as a result of this inability to speak, the patient is unable to communicate fully with the health care professional concerning his or her medical history or current symptoms. To compound this problem further, this inability to speak comes at a time when such medical information is often of vital importance.

Many techniques of communication have been substituted for speech in an effort to alleviate the anxiety of the patient and to facilitate health care delivery. These substitutes include lip reading, writing, and the use of hand signals. Unfortunately, few hospital staff people are able to lip read, and many times the ventilated patient lacks the strength or ability to write or use hand signals.

Communication can also be achieved through the use of artificial voicing systems. These systems typically include a sound generating device which produces a tone that is transmitted through a tube to the user's mouth and therein articulated into speech. This tone, therefore, takes the functional place of the user's vocal cords. Since speech is achieved with the patient articulating the tone into words in a normal manner, such speech systems have the advantage of being easily learned. However, since the tube must be positioned and held in the mouth, generally either by the patient or the health care professional, a problem is presented if the intubated patient lacks the physical ability to hold the tube in place. Furthermore, the health care professional may not have a free hand to devote to that job during all medical procedures.

A system for hands free operation is provided for by the Cooper-Rand intra oral speech device wherein the sound transmission tube is secured in place through attachment to either a headband or glasses worn by the patient. However, this additional mechanical support equipment requires time to be properly fitted to the patient and can be cumbersome for the patient to wear.

The Venti-Voice TM speech system also permits hands free operation through the use of a tone delivery tube that is inserted transnasally, allowing the tone to travel into the patient's oral cavity. This nasally held tube also prevents the inconvenience to the patient associated with the presence of a tube in their mouth while speaking and permits more accurate articulation of word sounds. However, the Venti-Voice TM system is primarily contemplated for use with tracheostomized patients. The separate nasally held tube can be awkward to use with an intubated patient wherein the endotracheal tube is also nasally inserted.

Certain artificial speech devices do not require a sound transmission tube. These hand held devices are placed against the patient's neck allowing the sound they produce to be projected through the neck tissue into the larynx and up towards the mouth. In addition to the problem of requiring a free hand for their operation, these devices are generally less effective than the tube systems in their ability to deliver a tone to the patient's mouth sufficient to produce audible speech. Various neck conditions, such as the presence of scar tissues or fat, can block the efficient transfer of sound through the neck. Furhermore, it takes more time for a patient to learn to use a neck held device to communicate effectively that it does for the patient to learn to use a tube speech system, and physically debilitated patients can find the use of neck held devices to be difficult or impossible.

SUMMARY

The present invention solves the problem of lack of speech in an intubated patient by incorporating into an endotracheal tube a means of conducting a tone to the patient's oral cavity. This tone is then formed into words by the patient through articulation in the usual manner.

The speaking endotracheal tube of the present invention is a tube, curved in shape, that contains both a primary ventilating channel for supplying air or oxygen to the lungs of the intubated patient, and a second speaking channel for the delivery of a tone to the patient's posterior oral pharynx.

The speaking channel runs parallel to and within the concave surface area of the tube's exterior wall. This tube wall area has been thickened in relation to the remainder of the exterior tube wall to accommodate the inclusion of the speaking channel. After considerable experimentation, a speaking channel design was discovered that provided satisfactory tone delivery ability and would allow for inclusion of such a channel, without significantly increasing the total cross sectional area of the resultant tube in comparison with the cross sectional area of conventional endotracheal tubes. Therefore, this speaking channel design made possible the combination of both a ventilating and tone delivery channel within a tube that can be easily inserted into a patient without causing patient discomfort in excess of that normally associated with an intubation. Furthermore, and more importantly, the speaking channel design permitted this combination of functions without significantly decreasing the air delivery capacity of the ventilating channel of the present invention in comparison with that of conventional endotracheal tubes.

The speaking channel terminates with an array of tone exit ports. These ports are holes contained in that portion of the thickened exterior wall area located directly over and bisecting the speaking channel. The exit ports are positioned on the tube such that when the tube is placed in the patient the ports are in air communication with the patient's posterior oral pharynx. The function of the exit ports is to deliver a tone or sound to the oral cavity which can therein be articulated into speech by the patient. Thus, since words are formed in the usual manner, most patients using the present invention are able to speak with little or no practice.

The tone or sound produced by a tone generator connected to the speaking channel through a small hollow flexible tube. This small inlet tube provides air communication between the generator and the speaking channel and is connected to a point on the tube that is exterior to the nasal pharynx when the tube is in place in the patient. This connection enables the tone to be propagated from the tone generator down the speaking channel to the tone exit ports.

The speaking endotracheal tube also contains a inflatable cuff for sealing between the patient's trachea and the tube, as is well known in the art, to substantially prevent the escape of air or oxygen, delivered to the lungs through the ventilating channel, from escaping up the trachea. Air for inflation of the cuff is delivered through a small channel contained within the exterior tube wall of the speaking endotracheal tube, as is also well known in the art.

The major advantages of the present invention over the prior art stem from the efficiencies of use that are obtained from combining the speaking and ventilatory functions into one tube. Upon insertion of the speaking endotracheal tube, both ventilating and speaking functions are provided for in an intubated patient more quickly and efficiently than with the use of a conventional endotracheal tube and a separate voicing system. Furthermore, this combination eliminates the need for a free hand or a mechanical support means to hold and position a separate speech device, as is required with other voicing systems.

The present invention, by not delivering the tone through an orally held tube, has the advantages of enhanced patient tolerance and improved word articulation as seen with the Venti-Voice TM system. But unlike that system, the present invention does not have the difficulties associated with the insertion of a separate, additional tube to provide for speech in an intubated patient.

Thus it is an object of the present invention to provide a novel speaking endotracheal tube.

It is further an object of the present invention to incorporate the speaking channel, within the endotracheal tube thereby allowing an efficient, hands free, quick method of providing speech for an intubated patient.

It is further an object of the present invention to provide for an easy and readily learned means of oral communication for the intubated patient.

It is further an object of the present invention to provide such a novel speaking endotracheal tube that maximizes material, is simple in design, and is easy and inexpensive to manufacture, assemble, and use.

These, and further objects and advantages of the present invention, will become clearer in light of the following detailed description.

DESCRIPTION OF THE DRAWINGS

The illustrative embodiments may best be described by reference to the accompanying drawings where.

DESCRIPTION OF THE PREFERRED EMBODIMENT

A speaking endotracheal tube, according to the teachings of the present invention, is shown in the figures and generally designated 10.

Figure 1:
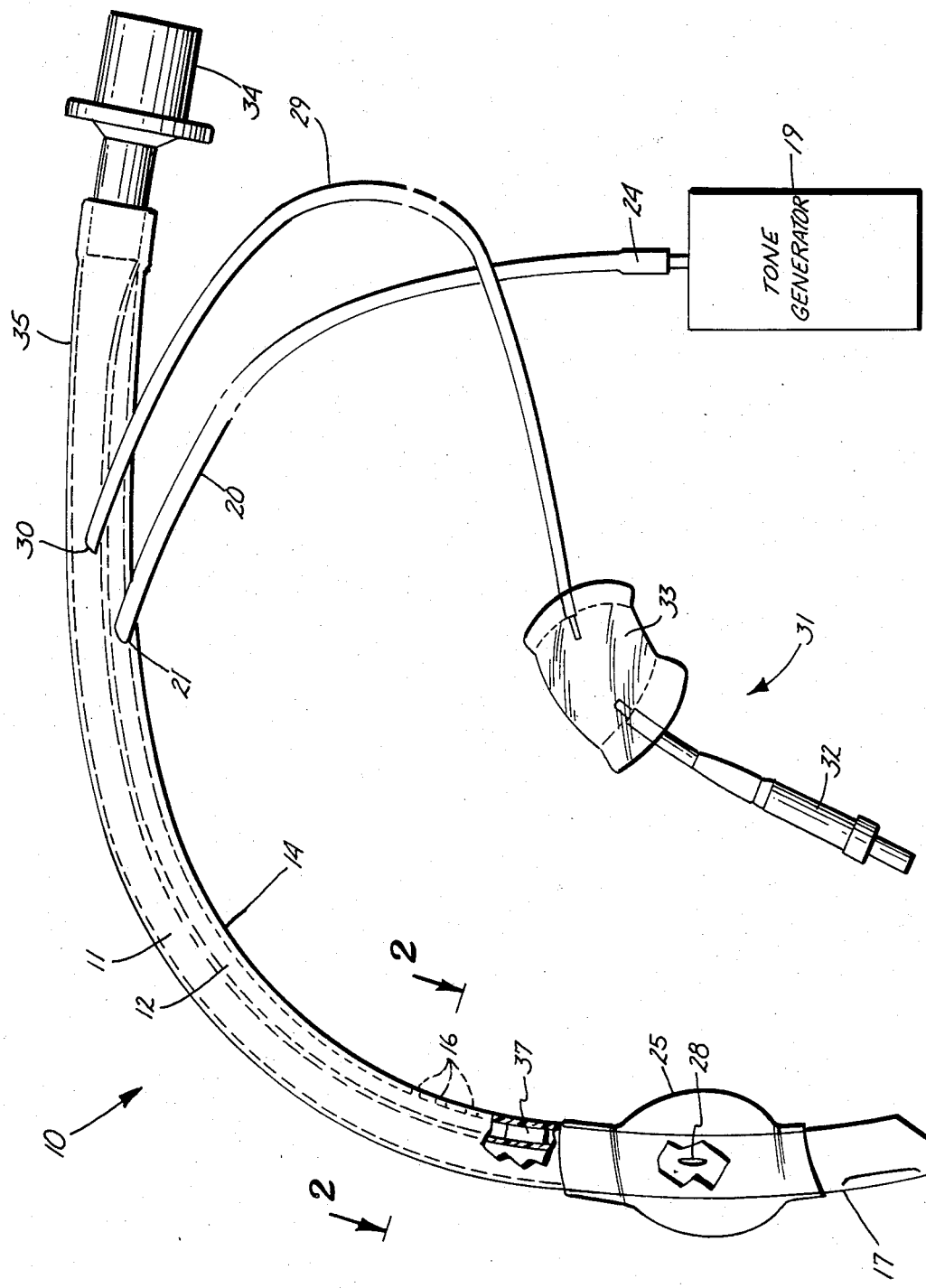
FIG. 1 shows a speaking endotracheal tube according to the teachings of the present invention.
Figure 2:
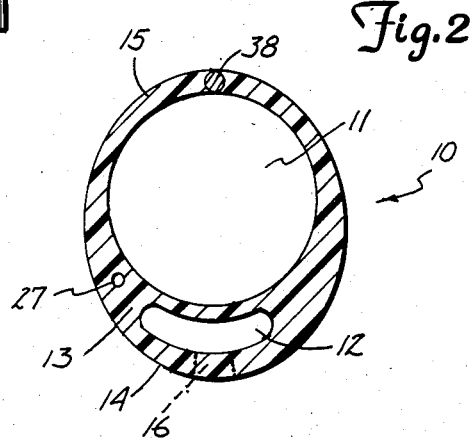
FIG. 2 shows a cross-sectional view of the speaking endotracheal tube of FIG. 1.

Tube 10 is an extruded tube made of a medical grade clear PVC that is flexible, but sufficiently rigid so that it does not collapse and so that it assumes the curved configuration, when in a relaxed condition, as is shown in FIG. 1. Tube 10 contains a primary ventilating channel 11 and a secondary speaking channel 12, as best seen in FIG. 2. Tube 10, as seen in the cross-sectional view of FIG. 2, has a thickened exterior wall area 13. Wall area 13 is wider than tube wall area 15, to accommodate inclusion of speaking channel 12. The majority of the cross-sectional area of tube 10 is used for ventilating channel 11. A smaller proportion of that area is devoted to speaking channel 12, as seen in FIG. 2. The cross-sectional shape of speaking channel 12, as seen in FIG. 2, can be described as a slightly curved elongated oval. Speaking channel 12 has a cross-sectional area of approximately 6.0 mm$^2$. Ventilating channel 11 has an inside diameter of from 6 to 8 mm.

Figure 3:
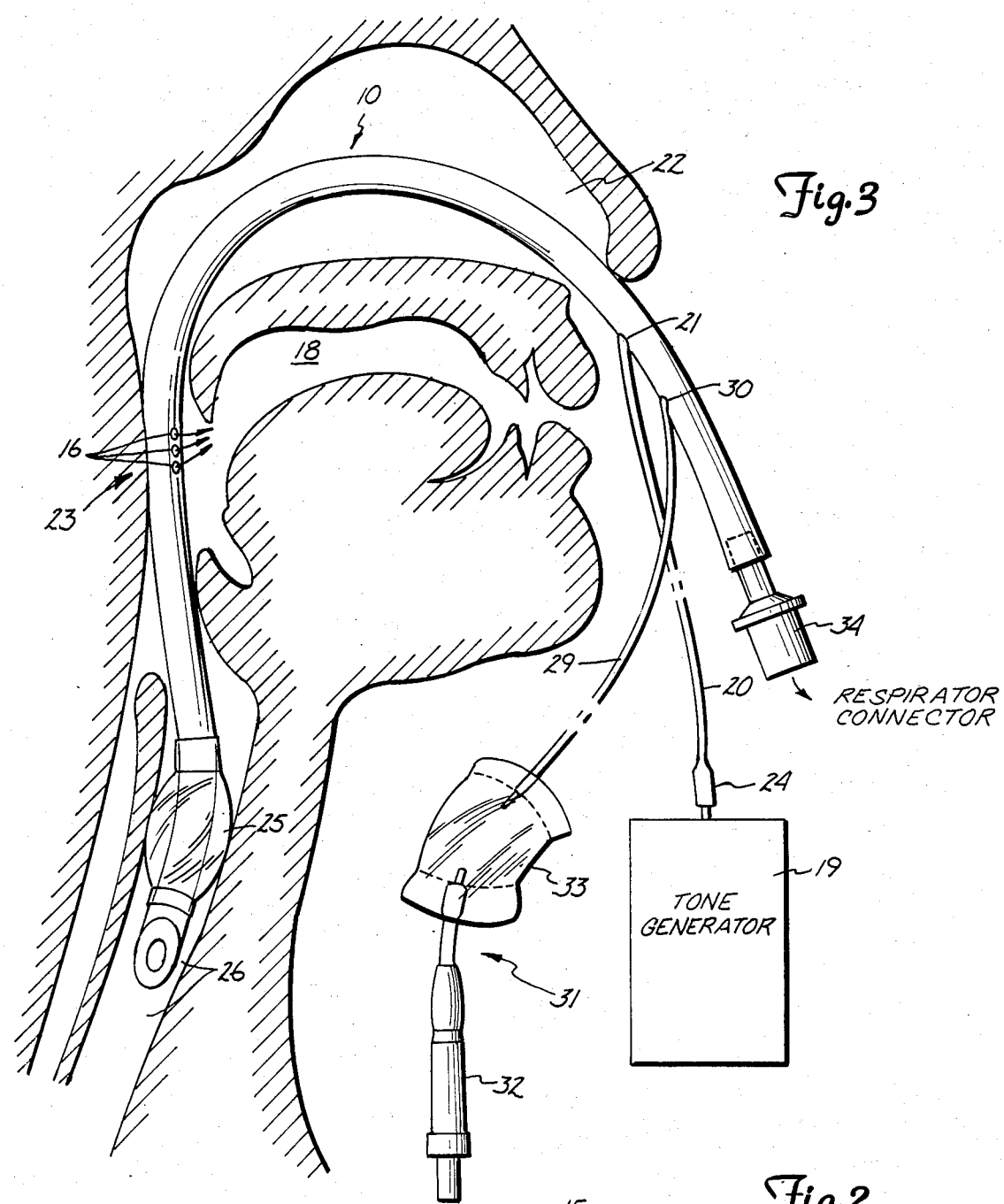
FIG. 3 shows a speaking endotracheal tube according to the teachings of the present invention as it may be located in the trachea of the patient.

Speaking channel 12 runs along concave surface 14 of tube 10, as seen in FIG. 1. Speaking channel 12 contains an array of tone exit ports 16, as seen in FIGS. 1 and 3. Tone exit ports 16 are located in tube wall area 13, bisecting speaking channel 12, as seen in FIG. 2. Speaking channel 12 contains three exit ports 16, approximately 3.0 mm in diameter and separated from each other by approximately 1 mm. Exit ports 16 are arranged in a single line along an axis which is parallel to the curved shape of tube 10 and bisects speaking channel 12, as seen in FIGS. 1 and 3. The array of tone exit ports 16 are centered approximately 13 cm from distal end 26 of tube 10.

Having described the essential features of the present invention, its operation can now be explained. In addition to the delivery of respiratory gas to a patient through ventilating channel 11, of the present invention, speaking channel 12 and tone exit ports 16 serve to deliver a tone to oral pharynx 18, that is therein articulated into speech by the patient. This tone is produced by tone generating means 19. Generator 19 can, for example, be of the eleectronic variety, an example of which is used in the Cooper-Rand speech device, or of the pneumatic reed type, an example of which is used in the Venti-Voice TM system. Tone generator 19 is connected to speaking channel 12, through speaking channel inlet tube 20, as seen in FIG. 1. Inlet tube 20 is a flexible, hollow plastic tube inserted into speaking channel 12 and joined, using a medically approved adhesive, to the surface of tube 10 at point 21, as seen in FIG. 1. This adhesive insertion technique, well known in the art, provides air communication between tone generator 19 and speaking channel 12, and also serves to block off that portion of speaking channel 12 proximal to the point of insertion of tube 20, thus maximizing the efficient delivery of the generated sound energy in a distal direction towards exit ports 16. Inlet tube 20 enters speaking channel 12 at a point on tube 10, exterior to nasal pharynx 22, when tube 10 is in place in the patient, as seen at point 21 in FIG. 3. Thus, the sound produced by tone generator 19 travels through inlet tube 20, and along speaking channel 12 to exit ports 16 where it enters the patient's posterior oral pharynx 23. The tone then enters oral pharynx 18 wherein it is articulated into speech by the patient. Quick releasable attachment of inlet tube 20 to tone generator 19 is accomplished with end connector 24, as seen in FIG. 1.

An inflatable cuff means 25, located on distal end 17 of tube 10, as seen in FIG. 1, is provided for sealing between tube 10 and trachea 26, of the intubated patient, as seen in FIG. 3, for substantially preventing air or oxygen, delivered to the lungs by ventilating channel 11, from escaping upwards through the trachea. Air for inflation of cuff 25 is delivered through cuff filling channel 27. Cuff filling channel 27 is located within tube wall area 13, as is seen in FIG. 2, and has an inside diameter of approximately 0.7 mm. An opening 28 is made through tube wall 13 into channel 27 to provide for air communication between channel 27 and the interior of cuff 25, as is well known in the art, and as seen in FIG. 1. Air is introduced to cuff filling channel 27 through cuff filling inlet tube 29. Inlet tube 29 provides air communication between, and connects cuff filling channel 27, to cuff filling assembly means 31, as seen in FIG. 1. Cuff filling inlet tube 29 is inserted into cuff filling channel 27 and joined, using a medically approved adhesive, to the surface of tube 10 at point 30, as seen in FIG. 1. The insertion of inlet tube 29 into cuff filling channel 27 block off that portion of channel 27 proximal to the point of entry of tube 29, thus all the air provided for inflation of cuff 25 is directed towards cuff 25. Inlet tube 29 enters cuff filling channel 27 at a point on tube 10 that is exterior to nasal pharynx 22 when tube 10 is in place in the patient, as seen at point 30 in FIG. 3. Cuff filling assembly 31 consists of stop valve 32 and pilot balloon 33. Pilot balloon 33 serves to indicate the level of inflation of cuff 25 and to detect deflation thereof, as is well known in the art. Stop valve 32 prevents deflation of cuff 25 and provides for releasable connection with an air supply, not shown, for inflation of cuff 25, as is also well known in the art.

Respirator connector 34 is a standard 15 mm connector and is inserted in proximal end 35 of tube 10 into ventilating channel 11, as seen in FIG. 1. Connector 34 is used for releasable connection to a line, now shown, of pressurized air or oxygen, for delivery of the air or oxygen to the patient's lungs through ventilating channel 11. Distal end 17 of tube 10 is cut on a bias, as seen at point 36 in FIG. 1, and is smoothly rounded in a convex contour, as is well known in the art, to facilitate entry of tube 10 into the body of the patient and minimize trauma to the patient's tissue. This rounding process also serves to seal off the distal end of cuff filling channel 27, to prevent air loss from cuff 25.

As a result of the manufacturing process of the present invention, speaking channel 12 runs along the entire length of tube 10. However, for efficient operation of the present invention, speaking channel 12 must be terminated at a point distal to exit ports 16. This blockage is accomplished with channel plug 37, as seen in FIG. 1. Plug 37, made of the same medical grade clear PVC material as tube 10, and secured in place using a medically approved adhesive, serves to maximize the delivery of sound energy through exit ports 16 into the patient's oral pharynx 18, by preventing the partial loss of this sound energy down speaking channel 12 and into the patient's trachea 26 that would result without plug 37. Plug 37 also serves to prevent the escape of air, delivered by ventilating channel 11, up speaking channel 12 and through exit ports 16, thereby preserving the sealing function of cuff 25.

Tube 10 also contains radiopaque line 38, which runs along the entire length of tube 10, and is located within exterior tube wall area 15 opposite from speaking channel 12, as seen in FIG. 2. Line 13 allows the precise position of tube 10, when it is in place in the patient, to be determined by an X-ray, as is well known in the art.

Certain specific structures embodying the present invention have been described herein. However, it will be apparent to persons skilled in the art that possible various modifications or rearrangements of the parts may be made without departing from the spirit and scope of the underlying inventive concept, and that the present invention is not limited to the particular forms herein shown and described except as indicated by the scope of the appended claims.

What is claimed is:

1. A speaking endotracheal tube for use in ventilating a patient, the endotracheal tube being insertable through a breathing cavity of a patient into a patient's trachea, the endotracheal tube comprising:
    (a) said endotracheal tube having a distal end adapted to be located within the trachea of a patient and a proximal end adapted to extend from said breathing cavity;
    (b) cuff means located proximate the distal end of said endotracheal tube for substantially preventing respiratory gases delivered to the lungs by the endotracheal tube from escaping around the tube upward in the trachea of the intubated patient
    (c) a primary ventilating channel contained within the endotracheal tube for the delivery of said respiratory gas to the lungs of an intubated patient; and
    (d) a secondary speaking channel contained within the endotracheal tube, separate from the ventilating channel, said secondary speaking channel having proximate one end thereof at least one tone exit port located between the proximal end of said endotracheal tube and said cuff means and adapter means at the opposite end thereof for interconnection to a tone generating means for the delivery of a tone to the posterior oral pharynx of an intubated patient enabling the patient to speak through articulation of the tone into speech.

2. The speaking endotracheal tube as defined in claim 1 which further comprises:
    (a) said cuff means comprises an inflatable cuff means located on the distal end of the tube and encircling an exterior wall of the tube; and
    (b) a cuff filling channel contained within the exterior wall of the tube, separate from the ventilating channel and the speaking channel, in air communication with the interior of the inflatable cuff means, to provide an interior channel along the tube for the delivery of inflation air to the cuff.

3. The speaking endotracheal tube as defined in claim 2 which further comprises:
    (a) a cuff filling assembly means, connected to and in air communication with the cuff filling channel, to provide air for the inflation of the cuff having a pilot balloon interconnected to the cuff filling channel for indicating the level of inflation of the cuff and a check valve interconnected to the cuff filling channel for maintaining the inflation of the cuff and for releasable connection with a cuff inflation air source.

4. A speaking endotracheal tube system for use in ventilating a patient which comprises:
    (a) an endotracheal tube being insertable through a breathing cavity of a patient into a patient's trachea, said tube having a proximal end adpated to extend from said breathing cavity and a distal end adapted to be located within the trachea of the patient, said tube having cuff means located proximate the distal end thereof for substantially preventing respiratory gases delivered to the lungs by the endotracheal tube from escaping around the upward in the trachea of the intubated patient;

(b) a primary ventilating channel contained within the endotracheal tube for the delivery of said respiratory gas to the lungs of an intubated patient;

(c) a secondary speaking channel contained within the endotracheal tube, separate from the ventilating channel, said secondary speaking channel having proximate one end thereof at least one tone exit port located between the proximal end of said endotracheal tube and said cuff means for the delivery of a tone to the posterior oral pharynx of an intubated patient enabling the patient to speak through articulation of the tone into speech; and (d) a tone generating means connected to and in air communication with the other end of the speaking channel for the generation of the tone delivered to the patient's posterior oral pharynx.

5. The speaking endotracheal tube system as defined in claim 4 which further comprises:

(a) said cuff means comprises an inflatable cuff means located on the distal end of the tube and encircling an exterior wall of the tube; and (b) a cuff filling channel contained within the exterior wall of the tube, separate from the ventilating channel and the speaking channel, in air communication with the interior of the inflatable cuff means, to provide an interior channel along the tube for the delivery of inflation air to the cuff.

6. The speaking endotracheal tube system as defined in claim 5 which further comprises:

(a) a cuff filling assembly means, connected to and in air communication with the cuff filling channel, to provide air for the inflation of the cuff having a pilot balloon means interconnected to the cuff filling channel for indicating a level of inflation of the cuff and a check valve interconnected to the cuff filling channel for maintaining the inflation of the cuff and for releasable connection with a cuff inflation air source.

7. An apparatus for use in ventilating a patient, comprising:

(a) endotracheal tube means for insertion through a breathing cavity of the patient into a patient's trachea, the endotracheal tube means having a distal end portion and a proximal end portion, the proximal end portion being accessible from outside the patient when the endotracheal tube means is so inserted into the patient's trachea, the endotracheal tube means having cuff means located proximate the distal end thereof for substantially preventing respiratory gases delivered to the lungs by the ventilating channel from escaping around the tube upward in the trachea of the intubated patient;

(b) the endotracheal tube means including primary ventilating channel means extending from proximate the proximal end portion to the distal end portion of the endotracheal tube means for delivery of respiratory gas to the lungs of the patient; and (c) the endotracheal tube means including secondary channel means having one end extending from proximate the proximal end portion of the endotracheal tube means and being separate from the primary ventilating channel means for delivery of a tone to the posterior oral pharynx of the patient enabling the patient to speak through articulation of the tone into speech, the secondary channel means including at least one exit port at the opposite end thereof located intermediate of the cuff means and the proximal end portion of the endotracheal tube means, and adapter means at said one end of said secondary channel means for interconnection to a tone generating means.

8. An apparatus in accordance with claim 7 further comprising:

(a) said cuff means comprises inflatable cuff means located proximate the distal end portion of the endotracheal tube means; and (b) cuff filling channel means extending from proximate the proximal end portion of the endotracheal tube means to the inflatable cuff emans for delivery of inflation air to the inflatable cuff means, the cuff filling channel means being in air communication with the inflatable cuff means, the cuff filling channel means being separate from the primary ventilating channel means and the secondary channel means.

9. An apparatus in accordance with claim 8, further including cuff filling assembly means interconnected to and in air communication with the cuff filling channel means for providing air for the inflation of the inflatable cuff means, the cuff filling assembly means having pilot ballon means interconnected to the cuff filling channel means for indicating the level of inflation of the inflatable cuff means and check valve means interconnected to the cuff filling channel means for maintaining the inflation of the inflatable cuff means and for releasable connection with a cuff inflation air source.

10. An apparatus in accordance with claim 7, further comprising tone generating means interconnected to and in air communication with the adapter means for the generation of the tone delivered to the patient's posterior oral pharynx.

11. An apparatus in accordance with claim 10, wherein said adapter means further comprising tube means integral with the endotracheal tube means for interconnecting the secondary channel means to the tone generating means.

12. An apparatus in accordance with claim 7, wherein the primary ventilating channel is encircled by an exterior wall of the endotracheal tube means, the secondary channel means being positioned in a thickened portion of the exterior wall.

13. An apparatus in accordance with claim 7, wherein the endotracheal tube means is flexible and assumes a curved configuration when in a relaxed condition.

14. An apparatus in accordance with claim 7, wherein the secondary channel means includes a plurality of exit ports.

15. An apparatus in accordance with claim 7, wherein the endotracheal tube means is an extruded one-piece tube.

16. An apparatus in accordance with claim 7, wherein the secondary channel means is terminated at a point distal to the tone exit port.

17. An apparatus in accordance with claim 7, wherein the endotracheal tube means further includes radiopaque line means extending along the endotracheal tube means in an exterior wall of the endotracheal tube means for locating the endotracheal tube means position.

18. An apparatus in accordance with claim 7, wherein the primary ventilating channel means has a larger diameter than the secondary channel means.

19. A method for ventilating a patient and enabling the patient to speak while being so ventilated, comprising the steps of:

(a) inserting endotracheal tube means having a distal end portion and a proximal end portion through a breathing cavity of the patient and into the patient's trachea, distal end portion first and sealing the distal end portion to the patient's trachea for substantially preventing respiratory gases delivered to the lungs by the endotracheal tube means from escaping around the tube means upward in the trachea of the intubated patient;

(b) delivering a respiratory gas to the lungs of the patient through a primary ventilating channel of the endotracheal tube means; and (c) delivering a tone to the posterior oral pharynx of the intubated patient through a secondary channel of the endotracheal tube means, separate from the primary ventilating channel, so as to enable the patient to speak through articulation of the tone into speech.

* * * * *

UNITED STATES PATENT AND TRADEMARK OFFICE
CERTIFICATE OF CORRECTION

PATENT NO. : 4,633,864

DATED : January 6, 1987

INVENTOR(S) : John J. Walsh

It is certified that error appears in the above-identified patent and that said Letters Patent is hereby corrected as shown below:

Title page, Under References Cited, Col. 1, Line 11, "3,443,964 5/1969 Oehmig" should be --3,443,564 5/1969 Oehmig--.
Title page, Under References Cited, Col. 2, Line 16, "4,378,796 4/1983 Milhand" should be --4,378,796 4/1983 Milhaud--.
Col. 2, Line 7, "Furhermore" should be --Furthermore--.
Col. 2, Line 9, "that" should be --than--.
Col. 2, Line 24, "second" should be --secondary--.
Col. 2, Line 62, after "sound" insert --is--.
Col. 3, Line 3, "a" should be --an--.
Col. 3, Line 17, after "for" insert --simultaneously. As a result, speech is provided for--.
Col. 4, Line 37, "eleectronic" should be --electronic--.
Col. 5, Line 16, "block" should be --blocks--.
Col. 5, Line 32, "now" should be --not--.
Col. 6, Line 67, after "around the" insert --tube--.
Col. 7, Line 34, "a" should be --the--.
Col. 8, Line 11, "emans" should be --means--.

Signed and Sealed this

Eleventh Day of April, 1989

*Attest:*

DONALD J. QUIGG

*Attesting Officer*

*Commissioner of Patents and Trademarks*